United States Patent [19]

Wright

[11] Patent Number: 5,078,267
[45] Date of Patent: Jan. 7, 1992

[54] PORTABLE CASE FOR CARRYING A SYRINGE WITH VARYING PLUNGER POSITIONS

[75] Inventor: Larry L. Wright, Houston, Tex.

[73] Assignee: LLW Enterprises, Inc., Houston, Tex.

[21] Appl. No.: 562,117

[22] Filed: Aug. 3, 1990

[51] Int. Cl.$^5$ ............................................. B65D 85/20
[52] U.S. Cl. .................................... 206/364; 206/571
[58] Field of Search ................ 206/364, 365, 571, 366

[56] References Cited

U.S. PATENT DOCUMENTS

| | | |
|---|---|---|
| 657,708 | 9/1900 | Rehmann ........................ 206/365 X |
| 685,091 | 10/1901 | Becton ................................ 206/365 |
| 1,280,607 | 10/1918 | Dudley . |
| 1,580,104 | 4/1926 | Hasselmann ........................ 206/366 |
| 1,625,035 | 4/1927 | Lilly ................................ 206/365 X |
| 1,711,594 | 5/1929 | Gillespie . |
| 1,718,701 | 6/1929 | O'Sullivan . |
| 1,838,825 | 12/1931 | Goldstein . |
| 2,023,289 | 12/1935 | Pringle . |
| 2,084,540 | 6/1937 | Smith ................................ 206/365 |
| 2,093,537 | 9/1937 | Balint ................................ 206/571 |
| 2,117,469 | 5/1938 | Woodyatt . |
| 2,720,969 | 10/1955 | Kendall ............................... 206/365 |
| 2,955,705 | 10/1960 | Kneger, Sr. et al. ................ 206/365 |
| 3,008,570 | 11/1961 | Roehr et al. ..................... 206/364 R |
| 3,272,322 | 9/1966 | Ogle . |
| 3,416,657 | 12/1968 | Sorensen, Jr. et al. ......... 206/365 X |
| 3,642,123 | 2/1972 | Knox .................................... 206/365 |
| 3,890,971 | 6/1975 | Leeson et al. ................... 206/365 X |
| 3,937,219 | 2/1976 | Karakashian . |
| 4,657,138 | 4/1987 | Watson ........................... 206/571 X |
| 4,671,408 | 6/1987 | Raines et al. ........................ 206/365 |
| 5,024,326 | 6/1991 | Sandel et al. ........................ 206/366 |

FOREIGN PATENT DOCUMENTS

| | | | |
|---|---|---|---|
| 99123 | 1/1925 | Austria .............................. 206/365 |
| 366105 | 1/1922 | Fed. Rep. of Germany ...... 206/364 |
| 670029 | 11/1929 | France .............................. 206/364 |
| 1408369 | 7/1965 | France .............................. 206/364 |
| 1502942 | 11/1967 | France .............................. 206/365 |
| 1200908 | 12/1985 | U.S.S.R. ............................ 206/366 |

Primary Examiner—Bryon P. Gehman
Attorney, Agent, or Firm—Rosenblatt & Associates

[57] ABSTRACT

The invention is a syringe carrying case which securely stabilizes the syringe while permitting the plunger to be withdrawn to specific pre-selected lengths to accommodate various size doses. The case holds a syringe with needle and dose therein. The case is attractively packaged to give the appearance of a pen which can be stuck in a pocket.

6 Claims, 2 Drawing Sheets

PORTABLE CASE FOR CARRYING A SYRINGE WITH VARYING PLUNGER POSITIONS

FIELD OF THE INVENTION

The field of this invention relates to a portable carrying case for syringes containing doses.

BACKGROUND OF THE INVENTION

Many persons who are afflicted with diabetes must take periodic shots of insulin. These shots are usually taken in conjunction with major meals of the day. Those that are on the go or in business need a convenient way to store syringes with pre-measured doses to be taken at periodic intervals.

In the past, various carrying cases have been proposed which do not accommodate a filled syringe. These types of cases are illustrated in U.S. Pat. Nos. 1,280,687; 1,711,594; and 1,718,701. Some cases include needles as part of the syringe assembly, with the needle dipped in a sterilizing fluid so that the dosage can be later added after the case is opened. Such a device is shown in U.S. Pat. No. 1,838,825. Yet others employ multi-tube carrying cases showing the syringe stored with the plunger out. Generally, these devices do not store syringes with doses and they provide spare needles and a swab. Typical of these is U.S. Pat. No. 2,023,289. U.S. Pat. No. 2,117,469 shows a reservoir at the bottom of the case to keep alcohol stored therein so that the needle remains in a sterile condition. U.S. Pat. No. 3,272,322 illustrates a throw-away assembly which shows the syringe housed in the container with the plunger out. This design does not contemplate storing a dose in the package but instead contemplates use in the operating room. U.S. Pat. No. 3,937,219 shows a container which stores a syringe with the plunger out with a predetermined dose of sterilized air to be injected into the patient during surgery. U.S. Pat. No. 4,671,408 is a folding container over a syringe which is stored in the container without a needle. The syringe is filled in advance. U.S. Pat. No. 4,524,888 relates generally to syringe carrying cases.

SUMMARY OF THE INVENTION

The invention is a syringe carrying case which securely stabilizes the syringe while permitting the plunger to be withdrawn to specific pre-selected lengths to accommodate various size doses. The case holds a syringe with needle and dose therein. The case is attractively packaged to give the appearance of a pen which can be stuck in a pocket.

DETAILED DESCRIPTION OF THE PREFERRED EMBODIMENT

Figure 1:
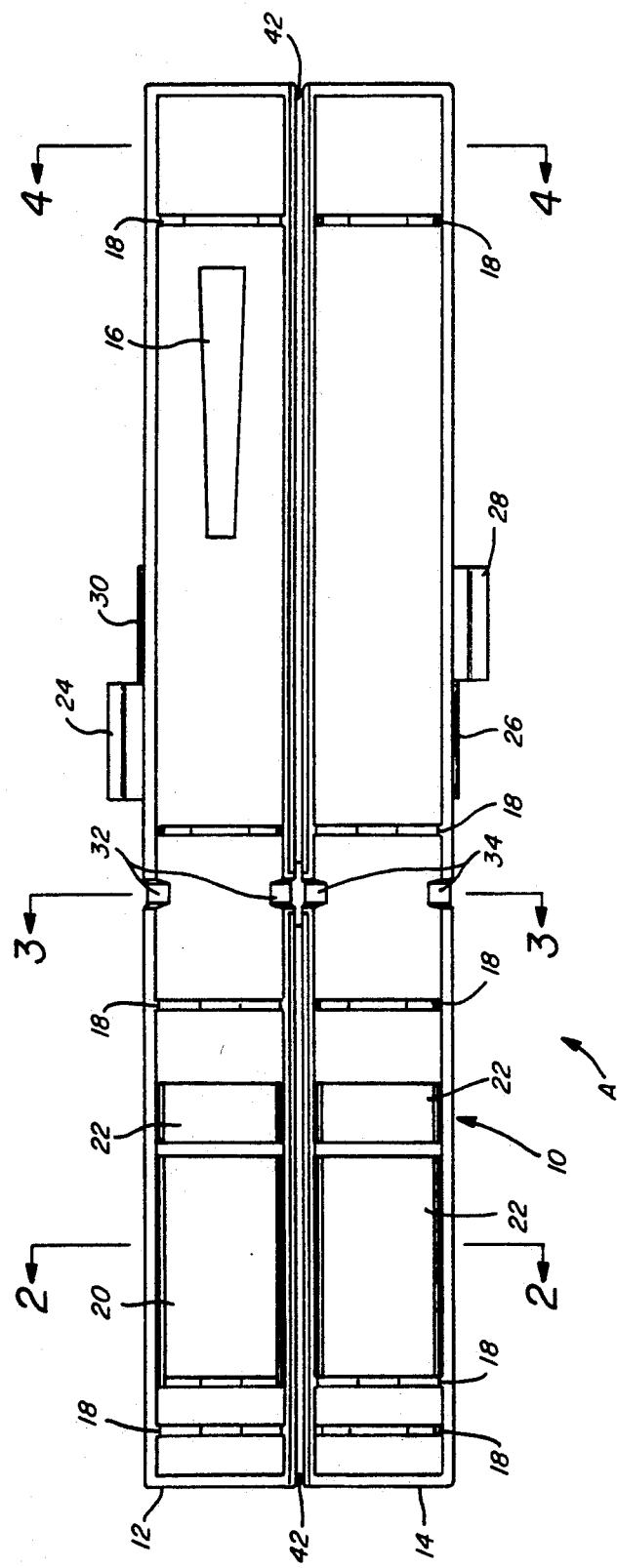
FIG. 1 is an elevational view of the outside of the carrying case shown in the open position.
Figure 4:
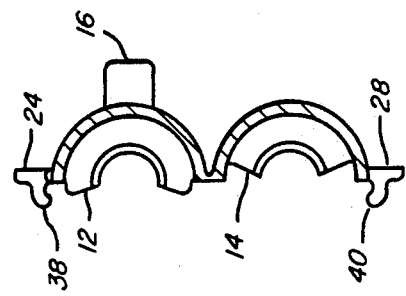
FIG. 4 is a sectional view of lines C—C of FIG. 1.
Figure 3:
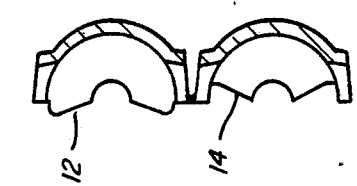
FIG. 3 is a sectional view at lines B—B of FIG. 1.
Figure 2:
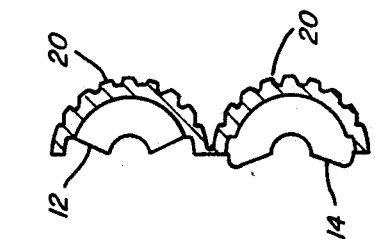
FIG. 2 is a sectional view at lines A—A of FIG. 1.

The apparatus A is shown in FIG. 1. The case is generally shown as 10 and consists of two halves 12 and 14. As seen in FIGS. 2-4, each of the two halves 12 and 14 are generally semicircular in shape so that the outline of the case 10 when closed is generally cylindrical. The outer surface treatment of halves 12 and 14 is such to make the case 10 appear to be a pen when it is placed in a patient's pocket. To this end, a clip 16 is attached to half 12. The final part of surface ornamentation is a series of longitudinal indentions parallel to each other, located in two fields and generally referred to as 20 and 22.

To keep half 12 secured to half 14, latch 24 secures to tang 26, while latch 28 secures to tang 30.

Both halves 12 and 14 contain opposing notches 32 and 34, respectively. Various other shapes of notches can be used to get the same result without departing from the spirit of the invention.

Figure 5:
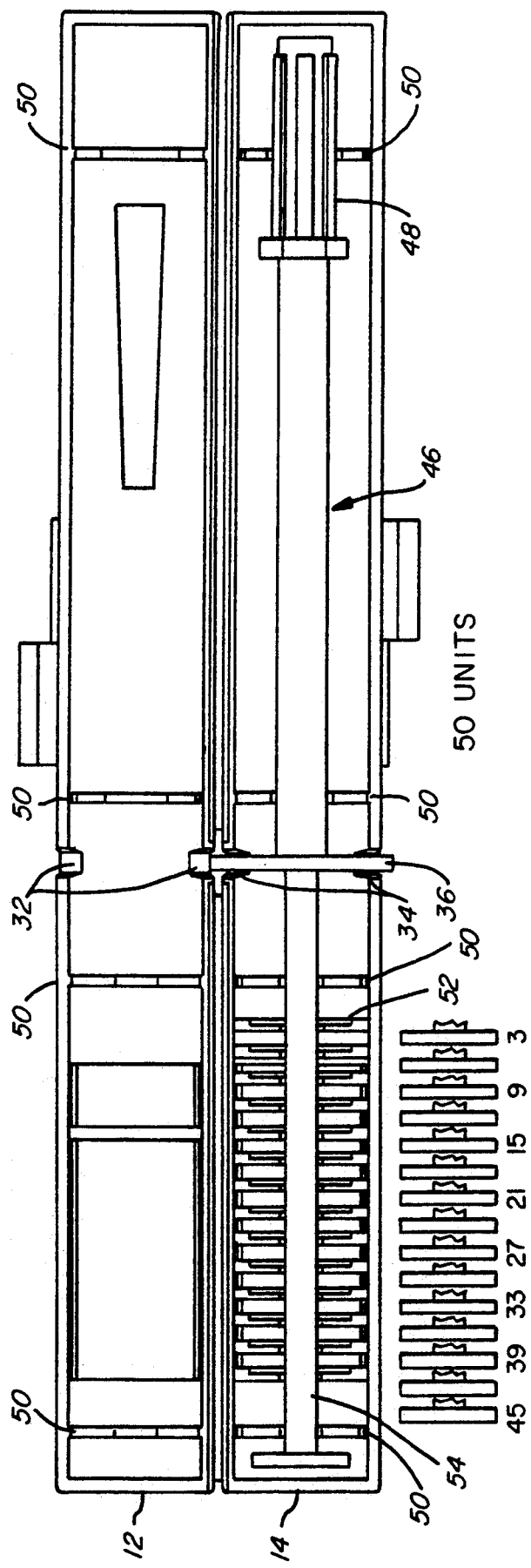
FIG. 5 is an elevational view of the inside of the carrying case shown in the open position.

These notches are useful for securing a flange 36 (see FIG. 5).

Both halves 12 and 14 contain opposing notched partitions 18 for stabilizing the plunger, body, and cap of the syringe, as can be noted in FIG. 5.

The preferred material for the case 10 is polypropylene and it can be made in any color desired. The details of the working of latch 24 are shown in part in FIG. 4. Latch 24 contains a projection 38 which engages tang 26. Similarly, latch 28 has a projection 40 which engages tang 30 to keep half 12 connected to half 14. When it is desired to open the case, latches 24 and 28 are activated, separating tangs 26 and 30 from projections 38 and 40.

Halves 12 and 14 are held together by an elongate member 42, which stretches for the substantial length of halves 12 and 14, only to be interrupted at notches 32 and 34 to allow flange 36 to extend through halves 12 and 14, as shown in FIG. 5. Member 42 serves as a hinge.

Referring now to FIG. 5, the internal construction of halves 12 and 14 is illustrated. Once again, FIG. 5 shows halves 12 and 14 but with a view opposite that of FIG. 1 so that the internals of the case 10 can be observed. Disposed within the case is a syringe 46, which is shown having a flange 36 extending through notches 32 and 34. The syringe 46 is fully assembled with a cap 48 over a needle which is not shown. The cap 48, body 46, and plunger 54 are supported by a saddles 50, as is the body of syringe 46 supported at flange 36. Internally, a plurality of saddles 52 are positioned at spaced intervals to fix the position of the plunger 54 at various positions to accommodate doses of different sizes. As shown in FIG. 5, the plunger is fully extended to accommodate the maximum dosage. The intermediate positions of the plunger are also shown in FIG. 5. The location of the saddles 52 can be determined depending upon the increments of dosages desired. There can also be a slight interference fit between the plunger 54 and the saddles 52 to stabilize the plunger and keep it from shifting. Similarly, saddles 50 can be constructed so that cap 48, body 46, and plunger 54 can snap into it to further stabilize the syringe 46. However, the extension of flange 36 into notches 32 and 34 laterally and longitudinally stabilizes the syringe body 46.

The foregoing disclosure and description of the invention are illustrative and explanatory thereof, and various changes in the size, shape and materials, as well as in the details of the illustrated construction, may be made without departing from the spirit of the invention.

I claim:

1. An apparatus for carrying a syringe with a dose, the syringe having a body, a plunger movable longitudinally into and out of the body, a needle, and a flange on the body, the apparatus comprising:

a reusable case comprising two portions and adapted to contain a said syringe;

hinge means hingedly joining said two portions to facilitate opening and closing of said case; and retaining means comprising at least one notch in said case for longitudinally retaining the flange on the body of a said syringe in a fixed position within said case when said case is in a closed position, the at least one notch allowing the flange of a said syringe to extend in part to the exterior of the case to facilitate visual determination that a said syringe is in the case without opening the case.

2. The apparatus of claim 1, wherein said case further comprises:

plunger retention means within said case for allowing the plunger of a said syringe to be selectively retained in a variety of positions with respect to the body of the syringe for use of the syringe with doses of varying size.

3. The apparatus of claim 2, wherein said plunger retention means further comprises a plurality of spaced apart saddles to cradle the plunger of a said syringe and retain it against substantial longitudinal movements.

4. An apparatus for carrying a syringe with a dose, the syringe having a body, a plunger movable into and out of the body, a needle, and a flange on the body, the apparatus comprising:

a reuseable case adapted to contain a said syringe;

retaining means comprising at least one peripheral notch in the case positioned so that the flange on a said syringe engages said at least one notch when said case contains the syringe and is closed, thereby retaining the body of the syringe in a fixed position within said case and the flange extends in part to the exterior of the case through said at least one notch to facilitate visual determination that the syringe is in the case without opening it;

means allowing movement of a first portion of said case away from a second portion of said case so as to allow the removal of a retained syringe from said at least one notch; and plunger retaining means comprising a plurality of spaced-apart saddles on the interior wall of said case to cradle the plunger of a contained said syringe selectively in a variety of positions to accommodate use of the syringe with doses of different sizes, said plunger retaining means also retaining the plunger of a contained said syringe against substantial longitudinal movements.

5. The apparatus of claim 4, wherein said case is made of two halves that when put together have a generally cylindrical shape, said halves further comprising:

means to selectively retain both halves of said case together in the closed position.

6. The apparatus of claim 5, further comprising:

a clip mounted to one of said halves to allow it to be secured to a pocket or article of wear;

surface ornamentation to make the visible surfaces of said halves take the appearance of a pen.

* * * * *

UNITED STATES PATENT AND TRADEMARK OFFICE
CERTIFICATE OF CORRECTION

PATENT NO. : 5,078,267
DATED : January 7, 1992
INVENTOR(S) : Larry L. Wright

It is certified that error appears in the above-identified patent and that said Letters Patent is hereby corrected as shown below:

COLUMN 1:

Line 56, please delete "A-A" and insert therefore --2-2--.

Line 57, please delete "B-B" and insert therefore --3-3--.

Line 58, please delete "C-C" and insert therefore --4-4--.

Signed and Sealed this

Fourth Day of May, 1993

Attest:

MICHAEL K. KIRK

Attesting Officer

Acting Commissioner of Patents and Trademarks